US010828055B2

(12) United States Patent
Berberich et al.

(10) Patent No.: US 10,828,055 B2
(45) Date of Patent: Nov. 10, 2020

(54) GUIDE AND PROTECTION ELEMENT FOR BONE REMOVAL INSTRUMENTS AND A BONE REMOVAL INSTRUMENT COMPRISING SAID ELEMENT

(71) Applicant: MEDACTA INTERNATIONAL SA, Castel San Pietro (CH)

(72) Inventors: Sascha Berberich, Castel San Pietro (CH); Francesco Siccardi, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 220 days.

(21) Appl. No.: 16/089,341

(22) PCT Filed: Mar. 8, 2017

(86) PCT No.: PCT/IB2017/051350
§ 371 (c)(1),
(2) Date: Sep. 27, 2018

(87) PCT Pub. No.: WO2017/168273
PCT Pub. Date: Oct. 5, 2017

(65) Prior Publication Data
US 2019/0125392 A1 May 2, 2019

(30) Foreign Application Priority Data
Mar. 31, 2016 (IT) .................. 102016000032872

(51) Int. Cl.
*A61B 17/00* (2006.01)
*A61B 17/32* (2006.01)
*A61B 90/00* (2016.01)

(52) U.S. Cl.
CPC ........ *A61B 17/32002* (2013.01); *A61B 90/08* (2016.02); *A61B 2090/08021* (2016.02); *A61B 2217/005* (2013.01)

(58) Field of Classification Search
CPC combination set(s) only.
See application file for complete search history.

(56) References Cited

U.S. PATENT DOCUMENTS

| 4,167,944 A | 9/1979 | Banko |
| 5,084,052 A * | 1/1992 | Jacobs ............. A61B 17/32002 606/170 |

(Continued)

FOREIGN PATENT DOCUMENTS

| JP | 63197445 A | 8/1988 |
| JP | H1-145053 A | 6/1989 |

OTHER PUBLICATIONS

International Search Report and Written Opinion for PCT Application No. PCT/IB2017/051350; dated Jul. 6, 2017; 13 pages.

(Continued)

*Primary Examiner* — Sameh R Boles
(74) *Attorney, Agent, or Firm* — Meunier Carlin & Curfman LLC

(57) ABSTRACT

A guide and protection element for bone removal instruments comprises a cylindrical body (2), suitable to be fitted over a bone removal instrument, having a first end (2a) that is completely open and a second end (2b) that is at least partially closed. The cylindrical body (2) is provided on a lateral surface (2c) with at least one window (5) to allow the bone removal instrument to operate on a bone to be treated.

10 Claims, 5 Drawing Sheets

(56) References Cited

U.S. PATENT DOCUMENTS

| | | |
|---|---|---|
| 5,529,580 A | 6/1996 | Kusunoki et al. |
| 5,569,284 A | 10/1996 | Young et al. |
| 2005/0240146 A1 | 10/2005 | Nash et al. |
| 2013/0172870 A1 | 7/2013 | Germain et al. |

OTHER PUBLICATIONS

English Translation of Notice of Reasons for Refusal issued in JP Application No. 2018-551363, dated Sep. 5, 2019.

\* cited by examiner

GUIDE AND PROTECTION ELEMENT FOR BONE REMOVAL INSTRUMENTS AND A BONE REMOVAL INSTRUMENT COMPRISING SAID ELEMENT

The present invention relates to a guide and protection element for a bone removal instrument.

The present invention also relates to a bone removal instrument comprising said guide and protection element.

Both objects of the present invention are of particular use in bone surgery, in particular in arthroscopic or open surgery, where the excision of osteophytes, bony protrusions or bone scar tissue is required.

The anatomical parts most prone to this pathology are, for example, the hip, the shoulder and the ankle, i.e., those parts of the body that are most easily injured.

The neck of the femur, for example, is a cylindrical structure that may, at times, have pathological bone spurs which need to be removed and could lead to femoral acetabular impingement.

During arthroscopic hip surgery, it may be necessary to remove a bony outgrowth in the area of the femoral head-neck junction.

Femoral acetabular impingement is caused by a series of congenital or acquired hip pathologies, the main pathogenic factor being abnormal contact between the two parts of the hip joint (the acetabulum and the proximal part of the femur).

It is important to eliminate this type of pathological or acquired impingement because it has been established that impingement is one of the most frequent causes of arthrosis of the hip joint.

Acquired impingement typically occurs as a result of bony outgrowths produced through trauma: it is a condition that affects athletes in particular.

This type of pathology can also affect other parts of the body, such as the shoulder, for example: in this case it is known as subacromial impingement.

In this specific pathology, the pain in the shoulder is usually due to a problem at the level of the rotator cuff tendons. Tendons are fibrous structures that attach the muscles to the bone.

The rotator cuff tendons are located between two bones within the shoulder.

Repeated microtrauma, a single contusion or even ordinary wear over the years contribute to a thickening of the tendons which gives rise to rubbing or impingement of the two bones.

Just like the femur and the shoulder, the ankle is also prone to sprains, repeated microtrauma or fractures which can give rise to what is known as fibrous impingement.

In all these cases, after a first diagnostic phase, the osteophyte or scar tissue must be removed surgically.

In the majority of cases, the surgical operation is performed using an arthroscopic procedure, which involves inserting the arthroscope and special instruments to excise the inflammatory or scar tissue and bony spurs. In particular, a small motorised instrument, generally a small cutter, is inserted to cut and draw out the excess portion of tissue.

Care must be taken to remove all of the excess bone without damaging the surrounding neurovascular structures or other soft tissue.

The cutter is only used under visual control, therefore the surgeon has no reference for determining the amount of bone that is removed. Incorrect assessment of the amount of bone that is removed could increase the duration of the surgical procedure or, on the contrary, entail the risk of making the remaining bone too thin.

From the inconveniences described above, it is clear that there is the need to provide a guide and protection device for a bone removal instrument that is able to remedy such problems.

As a matter of fact, one purpose of the present invention is to provide a guide and protection element that allows the bone removal instrument to be used in safety.

Another purpose of the present invention is to provide a guide and protection element for a bone removal instrument that protects the surrounding soft tissue which must not be damaged.

A further purpose of the present invention is to provide a guide and protection element for a bone removal instrument that provides a visual reference for the surgeon during the surgical procedure.

Lastly, a purpose of the present invention is to implement a bone removal instrument which allows the surgeon to perform the operation quickly and in safety, without any risk of injury to the patient.

In order to achieve the above purposes, the present invention discloses a guide and protection element for a bone removal instrument, the characteristic of which is set forth in Claim 1.

A further object of the present invention is a bone removal instrument, as disclosed in one of the appended claims.

Further advantageous characteristics are set out in the dependent claims. The present invention will now be described in greater detail, with reference to the accompanying drawings provided merely by way of example, in which:

Figure 1:
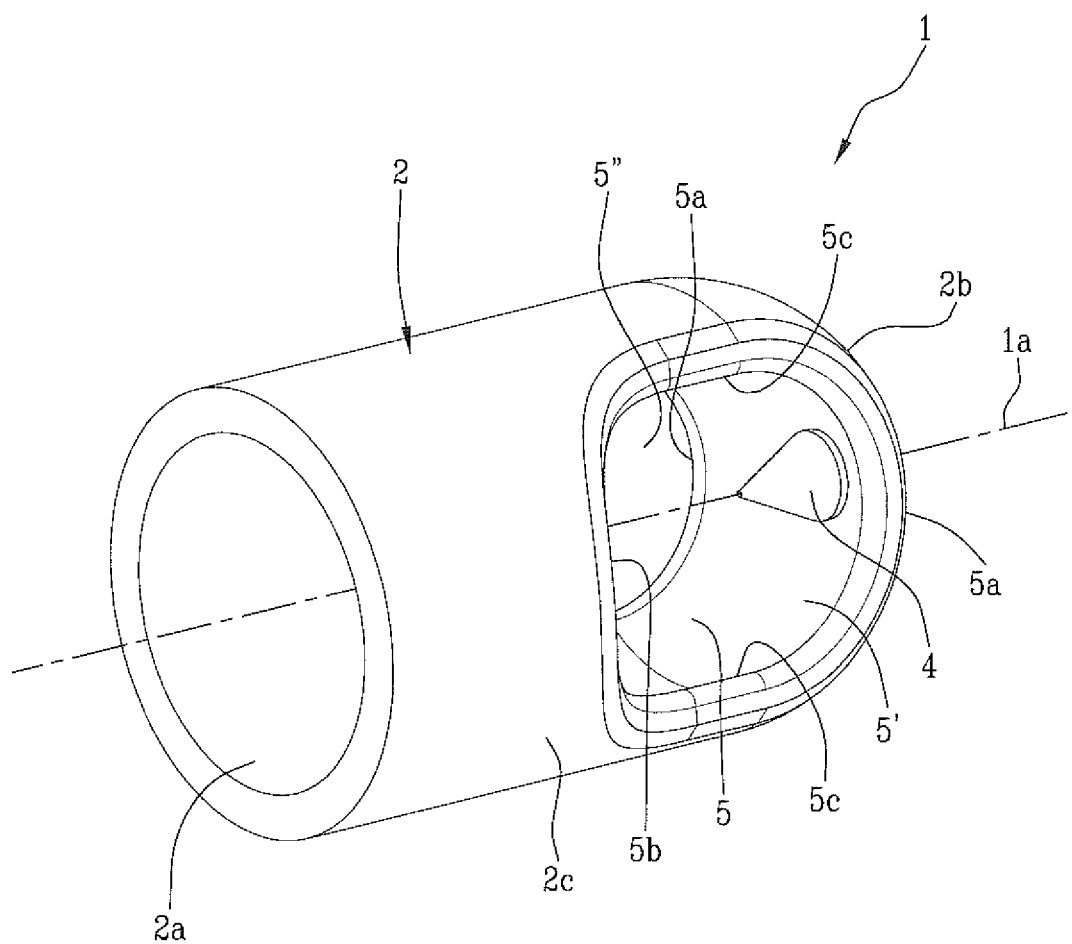
FIG. 1 shows a perspective view of a guide and protection element according to the present invention.

In the accompanying figures, reference numeral 1 generally indicates a guide and protection element for bone removal instruments.

Figure 4:
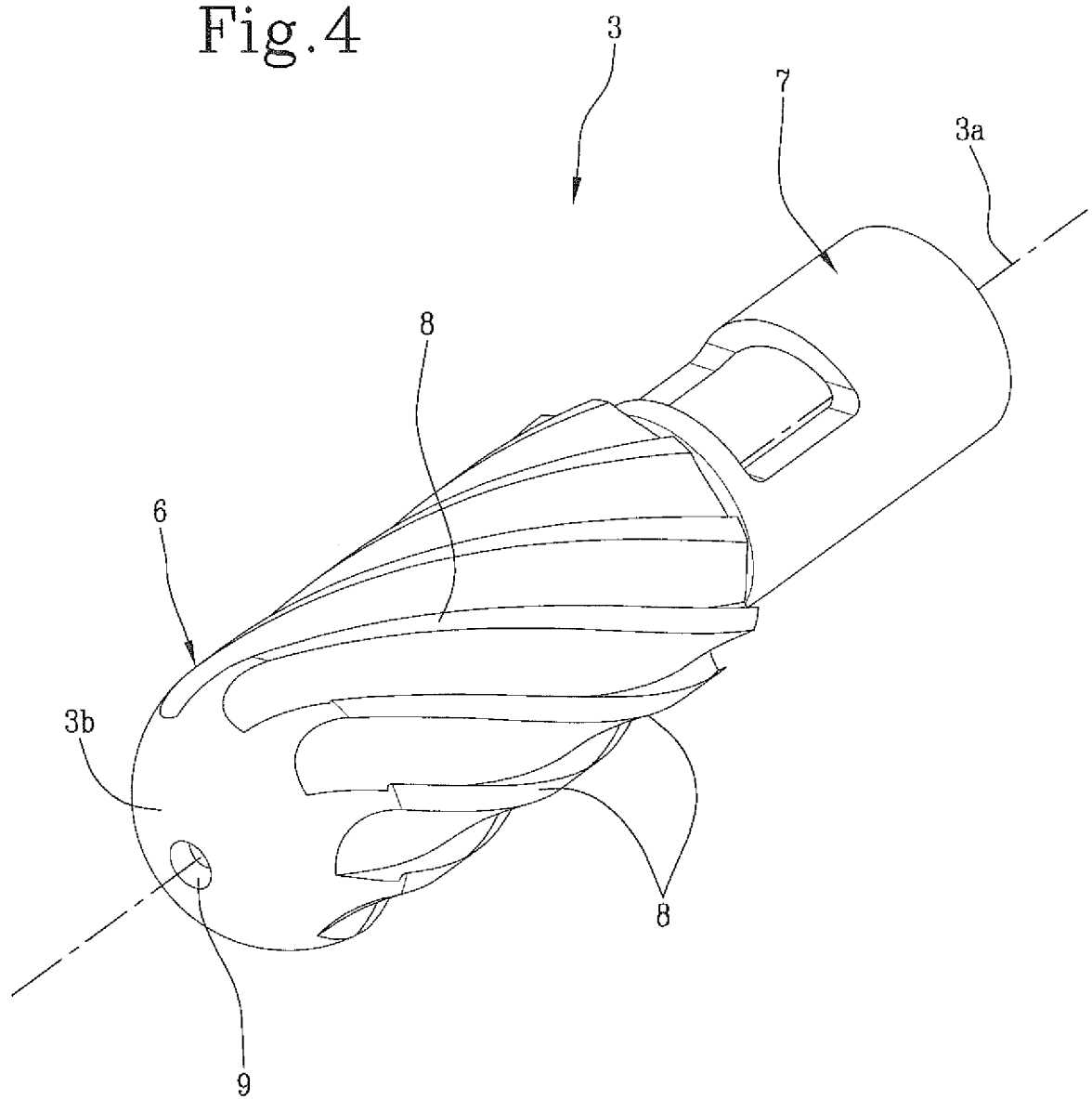
FIG. 4 is a perspective view of a bone removal instrument.
Figure 5:
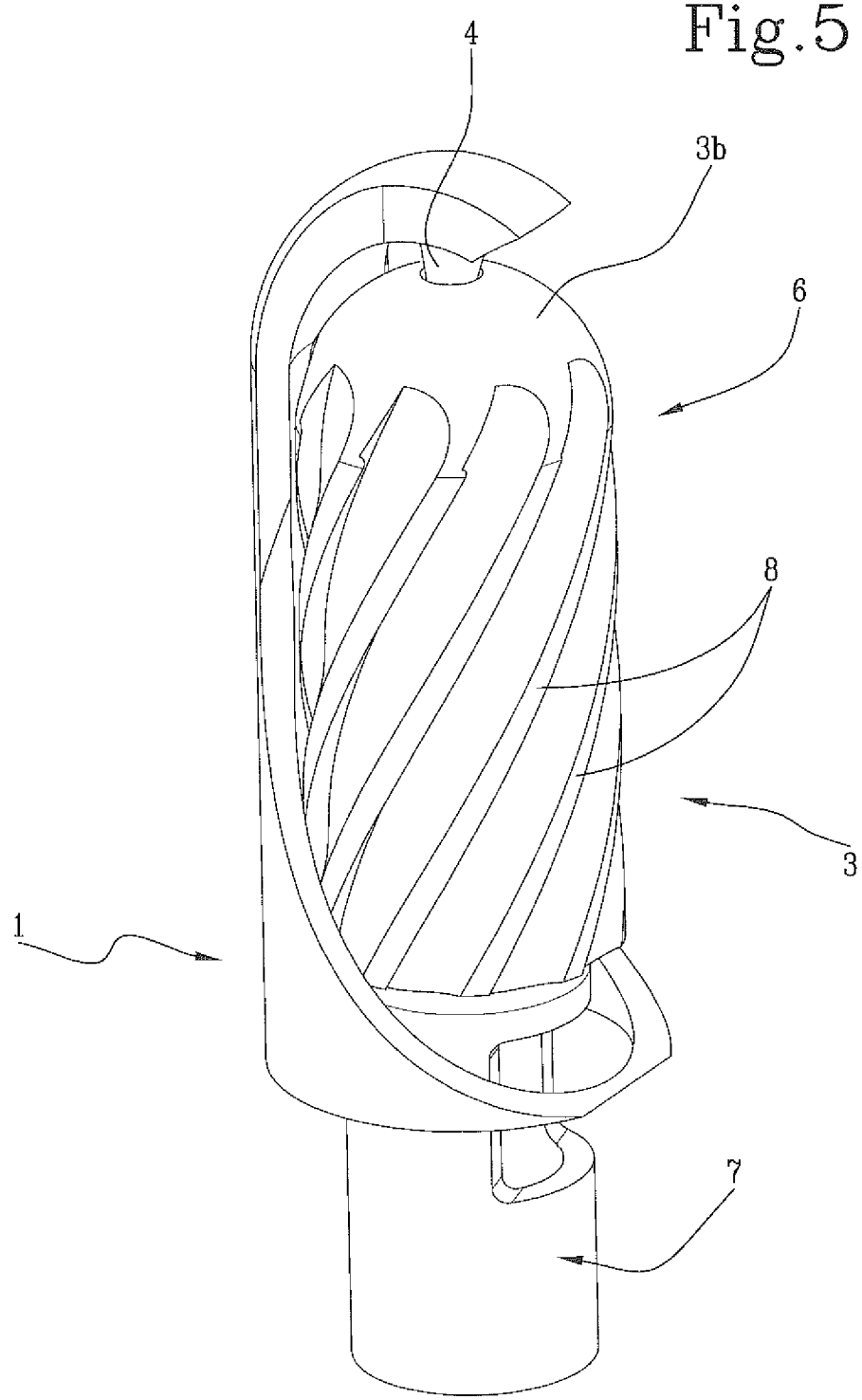
FIG. 5 is a perspective view of a bone removal instrument comprising the guide and protection element of FIG. 1.

Said guide and protection element 1 comprises a cylindrical body 2 suitable to be fitted over a bone removal instrument 3 of the type illustrated in FIG. 4.

The cylindrical body 2 has a first end 2a that is completely open, through which the bone removal instrument 3 is inserted, and a second end 2b that is at least partially closed, upon which the instrument abuts when it is fully inserted in the guide and protection element 1.

Inside the cylindrical body 2 there is a pin 4 that protrudes axially from the second end 2b and projects towards the first end 2a.

The pin 4 is aligned with a longitudinal axis 1a of the cylindrical body 2 and engages axially with the bone removal instrument 3.

In this way the guide and protection element 1 is connected to the instrument 3, the reciprocal axial alignment between the two is guaranteed and the instrument 3 is prevented from veering off course during its rotation about its longitudinal axis 3a.

The bone removal instrument 3 rotates with respect to the guide and protection element 1, which remains stationary while the former is being operated.

The cylindrical body 2 is provided, on one lateral surface 2c, with at least one window 5 interposed between the first end 2a and the second end 2b. The bone removal instrument 3 faces outwards through this window 5, at least partially, in particular a part of a cutting head 6 of the instrument, so that the cutting head 6 can operate on a bone to be treated in a controlled and guided manner.

In other words, the cutting head 6 is no longer completely exposed: only a part of it can interact with the bone.

The window 5 is delimited by an upper edge 5a, a lower edge 5b and two lateral edges 5c, which define abutment elements upon which the anatomical parts surrounding the part of bone to be removed rest, in addition to defining a visual reference for the surgeon.

Advantageously, the cylindrical body 2 is provided with at least two windows 5' and 5" on the lateral surface 2c, which are preferably arranged opposite to one another with respect to the axis 1a of the guide element 1. Advantageously, the two windows 5' and 5" differ from one another in size, in terms of their width and/or depth on the lateral surface 2c.

In other words, each window may be of a different size to the other in terms of their overall dimensions between the first 2a and the second 2b end of the cylindrical body.

Furthermore, the transverse dimensions may also be different and cover a greater or lesser circular sector on the lateral surface 2c.

In this latter case, the windows are also at a different depth from the lateral surface 2c towards the axis of the cylindrical body 1a. The plan view from above, from the second end 2b to the first end 2a, of one window 5' is different from the same plan view of the other window 5".

Therefore, the second end 2b may be asymmetrical with respect to the axis 1a of the cylindrical body 2. In other words, the distance d1 between the longitudinal axis 1a of the cylindrical body 2 and the upper edge 5a delimiting one window 5' is different from the corresponding distance d2 between the longitudinal axis 1a and the upper edge 5a delimiting the other window 5".

In this way, the cutting head 6 of the bone removal instrument 3 is exposed more through one window than the other.

This makes it possible to differentiate the cutting depth according to surgical requirements.

In an alternative configuration that is not illustrated, the windows may both have the same dimensions.

Figure 2:
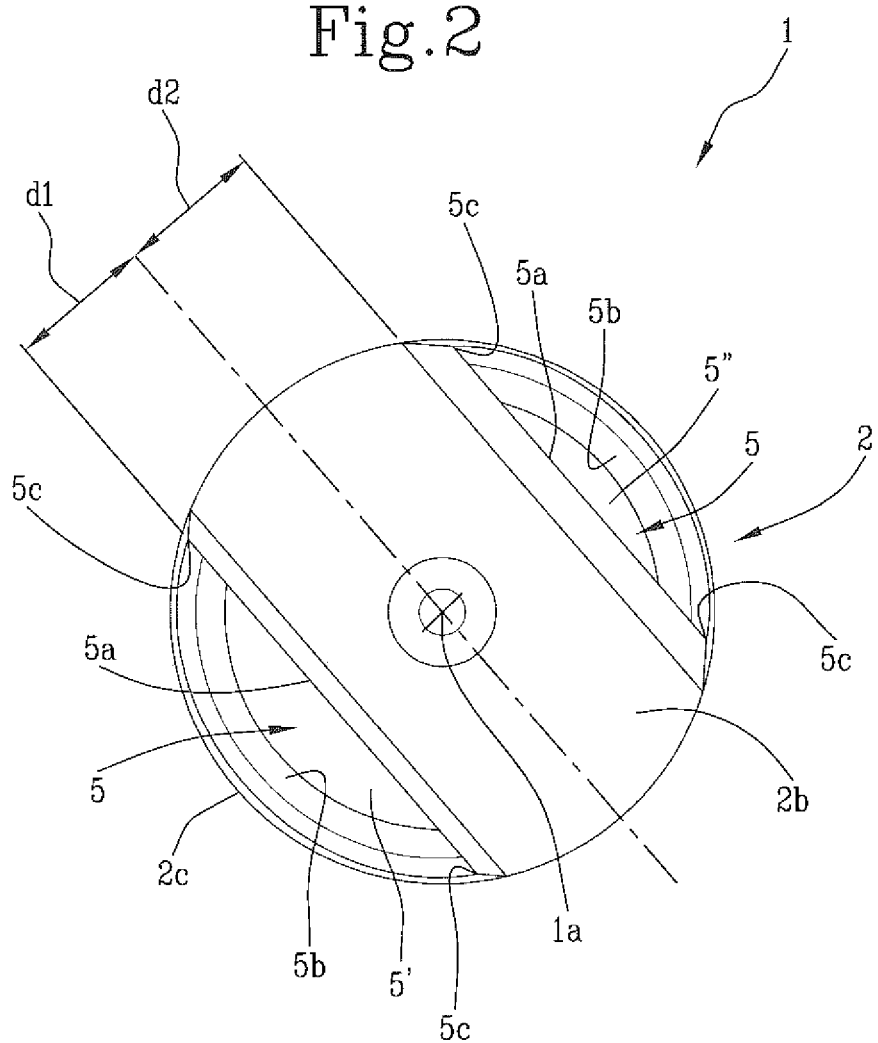
FIG. 2 shows a view from above of the guide and protection element illustrated in FIG. 1.

In the configuration illustrated in FIGS. 1 and 2, the cylindrical body 2 has a circular cross section.

Figure 3:
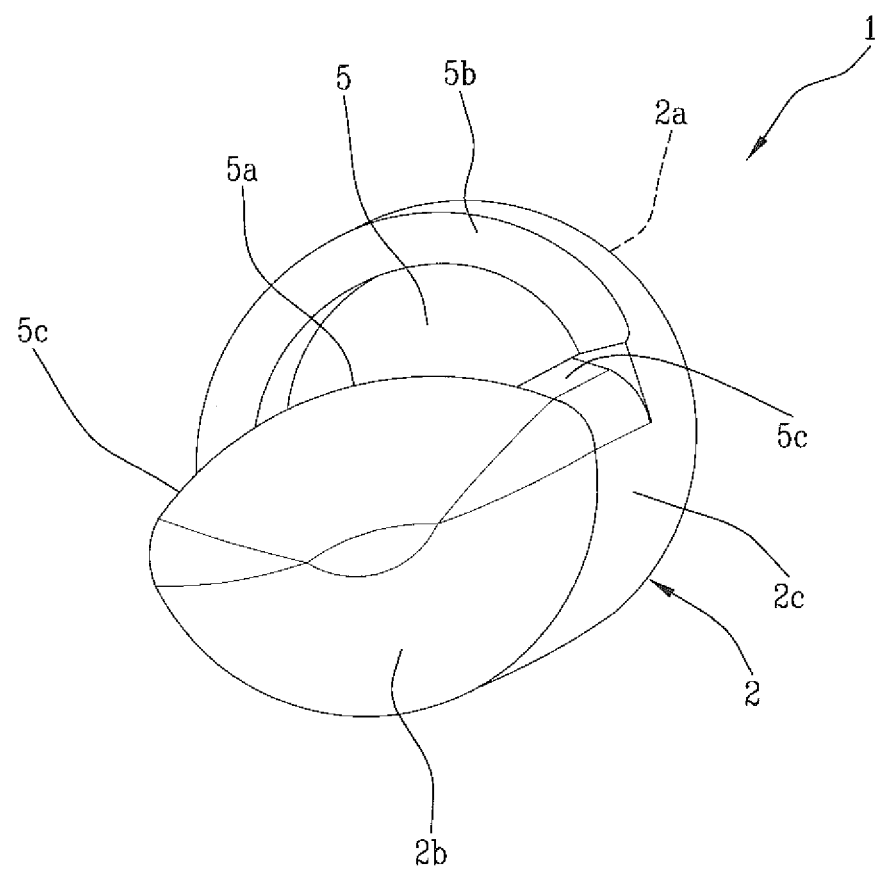
FIG. 3 is a perspective view of an alternative embodiment of the guide and protection element according to the present invention.

Alternative configurations are possible, such as that illustrated in FIG. 3 which shows a cylindrical body 2 with an elliptical cross section.

The bone removal instrument 3 is, preferably, a motorised rotary cutter. This instrument comprising a spindle 7 and a cylindrical cutting head 6 with circular cross section, having axially elongated blades 8 extending in a helical manner along the axial length of the cutting head 6.

At the top 3b, the cutting head 6 is provided with a seat 9 for inserting the pin 4 of the cylindrical body 2.

The bone removal instrument 3 further comprises an integrated suction system for the removal of unwanted bone tissue.

The guide and protection element 1 described above is fitted over the bone removal instrument 3 to protect the cutting head 6 and leave only a part thereof exposed. In particular, only the portion that interacts with the part of bone to be removed is exposed.

The edges 5a, 5b and 5c of each window 5' and 5" serve as an abutment element, beyond which the blade cannot cut.

The window 5 thus provides the surgeon with an accurate reference of the amount of bone that must be removed, thus avoiding excessive bone removal.

Furthermore, the guide and protection element 1 covers the part of blade that is not involved in the cutting, so as to protect surrounding anatomical parts, such as tendons, neurovascular structures or other soft tissue, which must not be cut.

The invention described herein achieves the proposed purposes and brings notable advantages.

The guide and protection element, as already mentioned, implements a visual reference for the surgeon, facilitating the phases of the surgical procedure.

Furthermore, the guide and protection element protects the area around the bone, eliminating the risk of accidental damage.

The bone removal instrument equipped with this guide and protection element is more manageable and allows the surgeon to operate in greater safety.

The invention claimed is:

1. A guide and protection element for bone removal instruments comprising a cylindrical body, suitable to be fitted over a bone removal instrument, having a first end that is completely open and a second end that is at least partially closed, said cylindrical body being provided on a lateral surface with at least one window to allow the bone removal instrument to operate on a bone to be treated; at the second end, an internal pin, facing towards the first end, aligned with a longitudinal axis of said cylindrical body; said pin engaging with the top of a bone removal instrument to fix said element to said instrument, prevent the instrument from veering off course and maintain the reciprocal axial alignment.

2. The guide and protection element as claimed in claim 1, characterized in that it is provided with at least two windows.

3. The guide and protection element as claimed in claim 2, characterized in that said two windows differ from one another in their dimensions and width.

4. The guide and protection element as claimed in claim 3, characterized in that the distance between a longitudinal axis of said cylindrical body and the upper edge delimiting one window is different from the distance between said longitudinal axis and the upper edge delimiting the other window.

5. The guide and protection element as claimed in claim 1, characterized in that said windows both have the same dimensions.

6. The guide and protection element as claimed in claim 1, characterized in that said cylindrical body has a circular cross section.

7. The guide and protection element as claimed in claim 1, characterized in that said cylindrical body has an elliptical cross section.

8. A bone removal instrument comprising a spindle, a cutting head characterized in that it comprises the guide and protection element as claimed in claim 1.

9. The bone removal instrument as claimed in claim 8, characterized in that said cutting head is a motorized rotary cutter.

10. The bone removal instrument as claimed in claim 8, characterized in that it comprises a suction system for the removal of unwanted bone tissue.

\* \* \* \* \*